United States Patent [19]

Nishimura et al.

[11] 4,367,332

[45] Jan. 4, 1983

[54] N$^4$-ALKOXYCARBONYLARABINOFURANOSYLCYTOSINE

[75] Inventors: Daikichi Nishimura; Toshiaki Sugawara, both of Fuji; Nobuyoshi Emoto, Numazu, all of Japan

[73] Assignee: Asahi Kasei Kogyo Kabushiki Kaisha, Japan

[21] Appl. No.: 282,227

[22] Filed: Jul. 10, 1981

[30] Foreign Application Priority Data

Jul. 16, 1980 [JP] Japan .................................. 55-97025

[51] Int. Cl.$^3$ ............................................. C07H 19/06
[52] U.S. Cl. ...................................... 536/23; 424/180
[58] Field of Search ........................... 424/180; 536/23

[56] References Cited

U.S. PATENT DOCUMENTS 3,975,367  8/1976  Gish et al. ............................. 536/23
3,991,045  11/1976  Ishida et al. .......................... 536/23

OTHER PUBLICATIONS

J. Medicinal Chemistry, 14(12) 1159–1162 (1971).

Chem. Pharm. Bull. 26(3) 981–984 (1978).

*Primary Examiner*—Johnnie R. Brown
*Attorney, Agent, or Firm*—Finnegan, Henderson, Farabow, Garrett & Dunner

[57] ABSTRACT

A N$^4$-alkoxycarbonylarabinofuranosylcytosine represented by the formula:

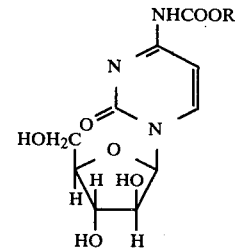

wherein R is an aliphatic hydrocarbon group having 4 to 22 carbon atoms.

These compounds are useful as anti-tumor agents.

9 Claims, No Drawings

$N^4$-ALKOXYCARBONYLARABINOFURANOSYL-CYTOSINE

BACKGROUND OF THE INVENTION

1. Field of the Invention

This invention relates to $N^4$-alkoxycarbonylarabinofuranosylcytosine which is a novel compound exhibiting excellent antitumor effect.

2. Description of the Prior Art

Arabinofuranosylcytosine represented by the formula:

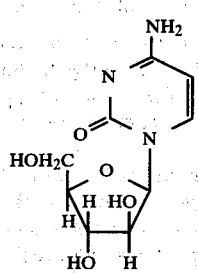

(I)

is useful and highly evaluated as an antitumor agent widely in clinical applications. But its effect can be exhibited only by non-oral adminstration and the compound suffers from the disadvantage of being ineffective by oral adminstration. This is considered to be due to the fact that said compound is changed to arabinofuranosyluracil having no antitumor effect by the action of deaminase existing in human bodies when it is absorbed through intestines.

The present inventors have made extensive studies to develop a derivative which will not lose its effect even by oral administration by overcoming the disadvantage of arabinofuranosylcytosine represented by the formula (I). Consequently, they have found that a novel compound having an amino group at the 4-position protected with an alkoxycarbonyl group has an excellent effect by oral administration to accomplish the present invention.

As a $N^4$-alkoxycarbonyl derivative of arabinofuranosylcytosine known in the art, there is only tri-haloethoxycarbonyl derivative as diclosed in J. Medicinal Chemistry, Vol. 14, No. 12, 1159-1162(1971). This is, however, a synthetic intermediate and there is no examination about its antitumor effect. The present compound is for the first time provided as a $N^4$-alkoxycarbonyl derivative for the purpose of oral administration.

SUMMARY OF THE INVENTION

The present invention provides a $N^4$-alkoxycarbonylarabinofuranosylcytosine represented by the formula:

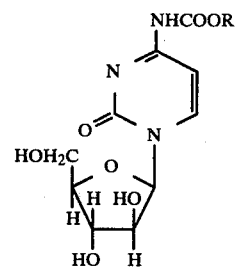

(II)

wherein R is an aliphatic hydrocarbon group having 4 to 22 carbon atoms.

Further, the present invention provides a novel antitumor agent containing the compound of the formula (II) as active ingredient.

DETAILED DESCRIPTION OF THE INVENTION

The aliphatic hydrocarbon group having 4 to 22 carbon atoms represented by R in the compound of the present invention may either be a straight-chin alkyl, preferably a $C_{7-17}$ straight-chain alkyl, a branched alkyl or a cycloalkyl. Typical examples may include n-butyl, n-pentyl, n-hexyl, n-heptyl, n-octyl, n-nonyl, n-decyl, n-undecyl, n-dodecyl, n-tridecyl, myristyl, n-pentadecyl, palmityl, n-heptadecyl, stearly, n-nonadecyl, n-eicosyl, n-heneicosyl, behenyl, isobutyl, isopentyl, isohexyl, isoheptyl, isooctyl, 2-ethylhexyl, cyclobutyl, cyclopentyl, cyclohexyl, cycloheptyl and others. More preferred groups are n-nonyl, n-undecyl, n-tridecyl and n-pentadecyl; isobutyl, isopentyl, isohexyl, isoheptyl, isooctyl and 2-ethylhexyl; cyclobutyl, cyclopentyl, cyclohexyl and cycloheptyl.

The compound of the present invention represented by the formula(II) can be prepared by allowing arabinofuranosylcytosine represented by the formula (I) to react with an alkoxycarbonyl halide represented by the formula: ROCOX (wherein R is the same as defined above and X a halogen atom) in the presence of a base. In this reaction, an alkoxycarbonyl halide, for example, an alkoxycarbonyl chloride or bromide, is used, for example, in an amount of equimolar or more, preferably in the range from 1 to 5 moles, per mole of arabinofuranosylcytosine. As the base, there may be employed an organic base such as pyridine, triethylamine or trimethylamine, or an inorganic base such as sodium carbonate, sodium hydrogen carbonate, potassium carbonate or potassium hydrogen carbonate. Such a base may be used in an amount at least equimolar, preferably 1 to 10 moles per mole of alkoxycarbonylhalide.

The reaction between arabinofuranosylcytosine and an alkoxycarbonyl halide may advantageously be carried out in a solvent. As such a solvent, there may suitably be used a solvent which can dissolve arabinofuranosylcytosine, typically a polar solvent such as dimethylformamide, dimethylacetamide, dimethylsulfoxide, etc. or a cyclic ether such as dioxane or tetrahydrofuran. It is also possible to use an alkoxycarbonyl halide as a solution dissolved in benzene, toluene or other solvents, if desired.

The reaction temperature may freely be chosen between the range from 0° C. to the boiling point of the solvent, but it is preferred to use a temperature in the range from 0° C. to 50° C. The reaction time, which depends on the alkoxycarbonyl halide employed, the solvent and the reaction temperature, may generally be in the range from 0.5 to 10 hours. The progress of the reaction can be traced by thin layer chromatography.

The desired product can be separated and purified from the thus prepared reaction mixture according to conventional procedures, for example, by removing the reaction solvent, dissolving the residue in a suitable solvent and reprecipitating from the resultant solution, followed further by recrystallization, if desired.

The thus prepared compound of the present invention is found to be powdery white solid, which has been confirmed to have the structure as represented by the formula (II) by elemental analysis and NMR.

The compound of the present invention is useful particularly as an antitumor agent for oral administration, since it can exhibit excellent antitumor effect even by oral adminstration.

The compound of the present invention is also found to be very stable as compared with $N^4$-acylarabinofuranosylcytosine as disclosed in Japanese Patent Publication 5678/1978 (U.S. Pat. No.3,991,045). Thus, the alkoxycarbonyl group is found to be better than acyl group as a protective group for the amino group at $N^4$-position to a great advantage in practical application.

The compound of the present invention represented by the formula (II) is a novel compound which has not been written in literatures and found to exhibit an excellent antitumor effect even by oral administration, as confirmed by the biological tests using mouse having transplanted cancer cells.

The compound of the present invention can be formulated in any desired form using conventional excipients such as granules, tablets, sugar-coated tablets, powders, aqueous solutions, etc.

The present invention is further illustrated with reference to the following Examples.

EXAMPLE 1

To a solution of 4.0 g of arabinofuranosylcytosine dissolved in 50 ml of dimethylacetamide, there are added 5.0 g of triethylamine and 3.37 g of butyloxycarbonyl chloride. The reaction is carried out by stirring the mixture at room temperature for 3 hours. After completion of the reaction, the solvent is evaoprated under reduced pressure. The residue is diluted with 20 ml of ethanol, followed by addition of 150 ml of petroleum ether. After the mixture is stirred at 0° to 5° C. for one hour, the resultant precipitates are collected by filtration. The precipitates are dissolved in 15 ml of methanol and then 100 ml of water is added to the resultant solution. The mixture is left to stand in a refrigerator and the precipitated crystals are filtered to give 2.8 g of $N^4$-butyloxycarbonyl-1-$\beta$-D-arabinofuranosylcytosine (Yield:50%).

Elemental analysis for $C_{14}H_{21}H_3O_7$: Calcd. (%): C 48.98; H 6.17; N 12.24; Found (%): C 49.17; H 6.32; N 12.30.

NMR (in DMSO-$d_6$) $\delta$ value: —CH$_3$ 0.94, —(CH$_2$)$_2$— 1.0–2.0, H$_2'$–H$_5'$ 3.4–4.4, —OCH$_2$ 4.14, H$_1'$ 6.08, H$_5$ 7.04, H$_6$ 8.08

EXAMPLE 2

Example 1 is repeated except that 3.37 g of isobutyloxycarbonyl chloride is used in place of butyloxycarbonyl chloride to obtain 2.5 g of $N^4$-isobutyloxycarbonyl-1-$\beta$-D-arabinofuranosylcytosine (Yield:45%).

Elemental analysis for $C_{14}H_{21}N_3O_7$: Calcd. (%): C 48.98; H 6.17; H 12.24; Found (%): C 49.11; H 6.34; N 12.15.

EXAMPLE 3

Example 1 is repeated except that 3.7 g of pentyloxycarbonyl chloride is used in place of butyloxycarbonyl chloride to obtain 3.2 g of $N^4$-pentyloxycarbonyl-1-$\beta$-D-arabinofuranosylcytosine (Yield:53%).

Elemental analysis for $C_{15}H_{23}N_3O_7$: Calcd. (%): C 51.50; H 6.35; N 11.50; Found (%): C 51.32; H 6.48; N 11.59.

NMR(DMSO-$d_6$) $\delta$ value: —CH$_3$ 0.90, —(CH$_2$)$_3$— 1.1–1.9, H$_2'$–H$_5'$ 3.6–4.3, —OCH$_2$ 4.14, H$_1'$ 6.10, H$_5$ 7.06, H$_6$ 8.10.

EXAMPLE 4

To a solution of 4.0 g of arabinofuranosylcytosine dissolved in 50 ml of dimethylacetamide, there are added 3.0 g of pyridine and 4.06 g of n-hexylchloroformate. The reaction is carried out by stirring the mixture at room temperature for 3 hours. After the reaction is over, dimethylacetamide is evaporated under reduced pressure. The residue is diluted with 100 ml of cold water and the mixture is stirred under ice-cooling for one hour. The precipitated solids are filtered and dried. The resultant white powders are washed with ethyl ether to obtain 2.9 g of $N^4$-hexyloxycarbonyl-1-$\beta$-D-arabinofuranosylcytosine (Yield:47%).

Elemental analysis for $C_{16}H_{25}N_3O_7$: Calcd. (%): C 51.75; H 6.79; N 11.31; Found (%): C 51.53; H 6.88; N 11.26.

NMR(DMSO-$d_6$) $\delta$ value: —CH$_3$ 0.88, —(CH$_2$)$_3$— 1.1–1.9, H$_2'$–H$_5'$ 3.3–4.3, —OCH$_2$— 4.12, H$_1'$ 6.10, H$_5$ 7.04, H$_6$ 8.08

EXAMPLE 5

Example 4 is repeated except that 4.06 g of cyclohexylchloroformate is used in place of n-hexylchloroformate to obtain 2.7 g of $N^4$-cyclohexyloxycarbonyl-1-$\beta$-D-arabinofuranosylcytosine (Yield:44%).

Elemental analysis for $C_{16}H_{23}N_3O_7$: Calcd. (%): C 52.03; H 6.28; N 11.38; Found (%): C 52.31; H 6.47, N 11.29.

EXAMPLE 6

To a solution of 4.0 g of arabinofuranosylcytosine dissolved in 50 ml of dimethylacetamide, there are added 4.15 g of sodium hydrogen carbonate and 4.41 g of heptylchloroformate. The resultant mixture is allowed to react under stirring at room temperature for 3 hours. After the reaction, dimethylacetamide is removed under reduced pressure and 150 ml of cold water is added to the residue. After the mixture is stirred for 2 hours, the solids are collected by filtration and dried. Recrystallization of the white powders obtained is performed twice, using 200 ml and 150 ml of a mixture of chloroform-acetonitrile (1:1), to give 2.5 g of $N^4$-heptyloxycarbonyl-1-$\beta$-D-arabinofuranosylcytosine (Yield:40%).

Elemental analysis for $C_{17}H_{27}N_3O_7$: Calcd. (%): C 52.98; H 7.06; N 10.90; Found (%): C 53.13; H 6.87; N 10.85.

NMR(DMSO-$d_6$) $\delta$ value: —CH$_3$ 0.88, —(CH$_2$)$_5$— 1.1–1.9, H$_2'$–H$_5'$ 3.4–4.3, —OCH$_2$— 4.16, H$_1'$ 6.12, H$_5$ 7.08, H$_6$ 8.12

EXAMPLE 7

Example 6 is repeated except that 4.8 g of octylchloroformate is used in place of heptylchloroformate to obtain 2.6 g of $N^4$-oxtyloxycarbonyl-1-$\beta$-D-arabinofuranosylcytosine (Yield:40%).

Elemental analysis for $C_{18}H_{29}N_3O_7$: Calcd. (%): C 54.12; H 7.32; N 10.52; Found (%): C 54.01; H 7.15; N 10.46.

NMR(DMSO-d$_6$) $\delta$ value: —CH$_3$ 0.88, —(CH$_2$)$_6$— 1.0–1.8, H$_2'$–H$_5'$ 3.5–4.2, —OCH$_2$— 4.12, H$_1'$ 6.08, H$_5$ 7.02 H$_6$ 8.06.

EXAMPLE 8

In 120 ml of dimethylacetamide, 6.0 g of arabinofuranosylcytosine is dissolved and to the resultant solution are added 4.15 g of sodium hydrogen carbonate and 7.66 g of nonyloxycarbonyl chloride. The mixture is then allowed to react under stirring at 20 to 25° C. for 2 hours. After the reaction, the solvent is removed under reduced pressure and the residue is dissolved in a small amount of ethanol. Water is then added to the resultant solution and the precipitated solids are collected by filtration, followed by drying. The white powders obtained are washed thoroughly with ethyl ether to obtain 3.8 g of $N^4$-nonyloxycarbonyl-1-$\beta$-D-arabinofuranosylcytosine (Yield:37%).

Elemental analysis for $C_{19}H_{31}N_3O_7$: Calcd. (%): C 55.19; H 7.56; N 10.16; Found (%): C 55.04; H 7.66; N 10.14.

NMR(DMSO-d$_6$) $\delta$ value: —CH$_3$ 0.84, —(CH$_2$)$_7$— 1.0–1.8 H$_2'$–H$_5'$ 3.5–4.3, —OCH$_2$— 4.10, H$_1'$ 6.06, H$_5$ 6.98, H$_6$ 8.02

EXAMPLE 9

Example 8 is repeated except that 8.0 g of decyloxycarbonyl chloride is used in place of nonyloxycarbonyl chloride to obtain 4.0 g of $N^4$-decyloxycarbonyl-1-$\beta$-D-arabinofuranosylcytosine (Yield:40%).

Elemental analysis for $C_{20}H_{33}N_3O_7$: Calcd. (%): C 56.19; H 7.78; N 9.83; Found (%): C 54.26; H 7.94; N 9.72.

NMR(DMSO-d$_6$) $\delta$ value: —CH$_3$ 0.88, —(CH$_2$)$_8$— 1.1–1.8, H$_2'$–H$_5'$ 3.5–4.3, —OCH$_2$— 4.12, H$_1'$ 6.08, H$_5$ 7.04 H$_6$ 8.08.

EXAMPLE 10

In 130 ml of dimethylacetamide, 7.3 g of arabinofuranosylcytosine is dissolved and to the resultant solution is added 40 ml of a toluene solution containing 7.56 g of sodium hydrogen carbonate and 7.0 g of undecyloxycarbonyl chloride. The mixture is then stirred at room temperature for 3 hours. After the reaction is over, the solvent is removed under reduced pressure and ice-water is added to the residue, whereby the cyrstals are precipitated. The crystals are filtered and washed with water, followed by sufficient drying. Recrystallization of the product is performed twice, using 80 ml of chloroform-n-hexane, to give 4.0 g of $N^4$-undecyloxycarbonyl-1-$\beta$-D-arabinofuranosylcytosine (Yield:30%).

Elemental analysis for $C_{21}H_{35}N_3O_7$: Calcd. (%): C 57.03; H 8.14; N 9.50; Found (%): C 56.88; H 8.31; N 9.37.

NMR(DMSO-d$_6$) $\delta$ value: —CH$_3$ 0.86, —(CH$_2$)$_9$— 1.1–1.8, H$_2'$–H$_5'$ 3.5–4.3, —OCH$_2$— 4.16, H$_1'$ 6.14, H$_5$ 7.08, H$_6$ 8.12.

EXAMPLE 11

Example 10 is repeated except that 7.5 g of dodecyloxycarbonyl chloride is used in place of undecyloxycarbonyl chloride to obtain 4.1 g of $N^4$-dodecyloxycarbonyl-1-$\beta$-D-arabinofuranosylcytosine (Yield:30%).

Elemental analysis for $C_{22}H_{37}N_3O_7$: Calcd. (%): C 58.00; H 8.19; N 9.22; Found (%): C 57.75; H 8.35; N 9.12.

NMR(DMSO-d$_6$) $\delta$ value: —CH$_3$ 0.88, —(CH$_2$)$_{10}$— 1.1–1.8, H$_2'$—H$_5'$ 3.5–4.3, —OCH$_2$— 4.12, H$_1'$ 6.08, H$_5$ 7.02, H$_6$ 8.06

EXAMPLE 12

To a solution of 7.5 g of arabinofuranosycytosine dissolved in 150 ml of dimethylacetamide, there is added 40 ml of a toluene solution containing 7.56 g of sodium hydrogen carbonate and 11.8 g of tridecyloxycarbonyl chloride. The mixture is then allowed to react at room temperature under stirring for 3 hours. After completion of the reaction, the solvent is removed under reduced pressure and the residue is washed with a mixture of chloroform-ether (1:2). Then, the residual solids are dried. The dried product is further washed thoroughly with water, followed by drying, to give 5.6 g of $N^4$-tridecyloxycarbonyl-1-$\beta$-D-arabinofuranosylcytosine (Yield:40%).

Elemental analysis for $C_{23}H_{39}N_3O_7$: Calcd. (%): 58.82; H 8.37; N 8.95; Found (%): 58.64, H 8.51; N 8.77.

NMR(DMSO-d$_6$) $\delta$ value: —CH$_3$ 0.88, —(CH$_2$)$_{11}$ 1.0–1.8 H$_2'$–H$_5'$ 3.5–4.3, —OCH$_2$— 4.10, H$_1'$ 6.08, H$_5$ 7.02, H$_6$ 8.04

EXAMPLE 13

Example 12 is repeated except that 12.1 g of myristyloxycarbonyl chloride is used in place of tridecyloxycarbonyl chloride to obtain 5.2 g of $N^4$-myristyloxycarbonyl-1-$\beta$-D-arabinofuranosylcytosine (Yield:35%).

Elemental analysis for $C_{24}H_{41}N_3O_7$: Calcd. (%): C 59.61; H 8.71; N 8.69; Found (%): C 59.82; H 8.57; N 8.73;

NMR(DMSO-d$_6$) $\delta$ value: —CH$_3$ 0.88, —(CH$_2$)$_{12}$— 1.1–1.8; H$_2'$–H$_5'$ 3.5–4.4, —OCH$_2$— 4.10, H$_1'$ 6.06, H$_5$ 7.02, H$_6$ 8.06.

EXAMPLE 14

Example 12 is repeated except that 12.5 g of pentadecyloxycarbonyl chloride is used in place of tridecyloxycarbonyl chloride to obtain 5.7 g of $N^4$-pentadecyloxycarbonyl-1-$\beta$-D-arabinofuranosylcytosine (Yield:37%).

Elemental analysis for $C_{25}H_{43}N_3O_7$: Calcd. (%): C 60.34; H 8.71; N 8.44; Found (%): C 60.52; H 8.65; N 8.57.

NMR(DMSO-d$_6$) $\delta$ value: —CH$_3$ 0.88, —(CH$_2$)$_{13}$— 1.1–1.8, H$_2'$–H$_5'$ 3.5–4.4, —OCH$_2$— 4.12, H$_1'$ 6.04, H$_5$ 7.02, H$_6$ 8.04.

EXAMPLE 15

A toluene solution containing 1.8 g of palmityloxycarbonyl chloride is added to 20 ml of a dimethylacetamide solution containing 1.5 g of arabinofuranosylcytosine and 1.7 g of sodium hydrogen carbonate. The reaction is carried out at room temperature with stirring of the mixture for 3 hours. After the reaction is completed, the reaction mixture is poured into an ice-water and the precipitated solids are collected by filtration, followed by washing successively with acetone and with hot chloroform. The resultant solids are dissolved in a mixture of chloroform-methanol and then subjected once to filtration, followed by removal of the solvent. The residue is subjected to crystallization from n-hexane to give 0.92 g of $N^4$-palmityloxycarbonylarabinofuranosylcytosine (Yield:30%).

Elemental analysis for $C_{26}H_{45}N_3O_7$: Calcd. (%): C 61.03; H 8.86; N 8.21; Found (%): 61.27; H 8.65; N 8.19.

NMR(DMSO-$d_6$) $\delta$ value: —$CH_3$ 0.88, —$(CH_2)_{14}$— 1.1–1.8, $H_2'$–$H_5'$ 3.5–4.4, —$OCH_2$— 4.20, $H_1'$ 6.22, $H_5$ 7.20, $H_6$ 8.24.

EXAMPLE 16

Example 15 is repeated except that 2.2 g of heptadecyloxycarbonyl chloride is used in place of palmityloxycarbonyl chloride to obtain 0.96 g of $N^4$-heptadecyloxycarbonyl-1-$\beta$-D-arabinofuranosylcytosine (Yield:30%).

Elemental analysis for $C_{27}H_{47}N_3O_7$: Calcd. (%): C 61.69; H 9.01; N 7.99; Found (%): C 61.46; H 9.23; N 7.85.

NMR(DMSO-$d_6$) $\delta$ value: —$CH_3$ 0.86, —$(CH_2)_{15}$— 1.0–1.8, $H_2'$–$H_5'$ 3.3–4.3, —$OCH_2$— 4.20, $H_1'$ 6.22, $H_5$ 7.20 $H_6$ 8.26.

EXAMPLE 17

Example 15 is repeated except that 2.5 g of stearyloxycarbonyl chloride is used in place of palmityloxycarbonyl chloride to obtain 1.2 g of $N^4$-stearyloxycarbonyl-1- $\beta$-D-arabinofuranosylcytosine (Yield:35%).

Elemental analysis for $C_{28}H_{49}N_3O_7$: Calcd. (%): C 62.31; H 9.15; N 7.79; Found (%): C 62.48; H 9.37; N 7.61.

NMR(DMSO-$d_6'$ 50° C.) $\delta$ value: —$CH_3$ 0.88, —$(CH_2)_{16}$— 1.0–1.8, $H_2'$–$H_5'$ 3.5–4.3, —$OCH_2$— 4.14, $H_1'$ 6.12, $H_5$ 7.04, $H_6$ 8.08.

EXAMPLE 18 to a solution of 2.43 g of arabinofuranosylcytosine dissolved in 40 ml of dimethylacetamide, there is added 10 ml of a toluene solution containing 3.0 g of potassium hydrogen carbonate and 5.8 g of behenyloxycarbonyl chloride. The reaction is carried out at room temperature with stirring of the mixture for 4 hours. After completion of the reaction, the mixture is poured into icewater and the precipitated solids are collected by filtration, followed by washing successively with acetone and with chloroform. The white solids obtained are dissolved in a mixture of chloroform-methanol and the resultant insolubles are filtered off. After removal of the solvent, the rersidue is subjected to precipitation from chloroform to obtain 2.0 g of $N^4$-behenyloxy-1-$\beta$-D-arabino-furanosylcytosine (Yield:35%).

Elemental analysis for $C_{32}H_{57}N_3O_7$: Calcd. (%): C 64.51; H 9.64; N 7.05; Found (%): C 64.63; H 9.42; N 7.14.

NMR(DMSO-$d_6$'50° C.) $\delta$ value: —$CH_3$ 0.88, —$(CH_2)_{20}$— 1.0–1.8, $H_2'$–$H_5'$ 3.5–4.3, —$OCH_2$— 4.12, $H_1'$ 6.10, $H_5$ 7.04, $H_6$ 8.08.

EXAMPLE 19

Example 18 is repeated except that 5.2 g of nonadecyloxycarbonyl chloride is used in place of behenyloxycarbonyl chloride to obtain 1.8 g of $N^4$-nonadecyloxycarbonyl-1-$\beta$-D-arabinofuranosylcytosine (Yield:32%).

Elemental analysis for $C_{29}H_{51}N_3O_7$: Calcd. (%): C 62.90; H 9.28; N 7.59; Found (%): C 62.76; H 9.41; N 7.62.

NMR(DMSO-$d_6$'50° C.) $\delta$ value: —$CH_3$ 0.88, —$(CH_2)_{17}$— 1.0–1.8, $H_2'$–$H_5'$ 3.5–4.2, —$OCH_2$— 4.14, $H_1'$ 6.08, $H_5$ 7.06, $H_6$ 8.06.

EXAMPLE 20

Example 18 is repeated except that 5.4 g of eicosyloxycarbonyl chloride is used in place of behenyloxycarbonyl chloride to obtain 1.7 g of $N^4$-eicosyloxycarbonyl-1-$\beta$-D-arabinofuranosylcytosine (Yield:30%).

Elemental analysis for $C_{30}H_{53}N_3O_7$: Calcd. (%): C 63.46; H 9.41; N 7.40; Found (%): C 63.67; H 9.70; N 7.22.

NMR(DMSO-$d_6$'50° C.) $\delta$ value: —$CH_3$ 0.88, —$(CH_2)_{18}$— 1.0–1.8, $H_2'$–$H_5'$ 3.5–4.3, —$OCH_2$— 4.12, $H_1'$ 6.04, $H_5$ 7.06 $H_6$ 8.04.

EXAMPLE 21

Example 18 is repeated except that 5.6 g of heneicosyloxycarbonyl chloride is used in place of behenyloxycarbonyl chloride to obtain 2.0 g of $N^4$-heneicosyloxycarbonyl-1-$\beta$-D-arabinofuranosylcytosine (Yield:35%).

Elemental analysis for $C_{31}H_{55}N_3O_7$: Calcd. (%): C 64.00; H 9.53; N 7.22; Found (%): C 64.28; H 9.75; N 7.38.

NMR(DMSO-$d_6$'50° C.) $\delta$ value: —$CH_3$ 0.88, —$(CH_2)_{19}$— 1.0–1.8, $H_2'$–$H_5'$ 3.5–4.3, —$OCH_2$— 4.14, $H_1'$ 6.06, $H_5$ 7.04, $H_6$ 8.06.

Biological tests

For the purpose of testing the antitumor effects of the compounds $N^4$-alkoxycarbonyl-arabinofuranosylcytosines prepared according to the present invention, there are employed CDF$_1$- strain male mice, five for each goup, and 200,000 cells of L-1210 (a kind of leukemic cell of mouse) are transplanted abdominally to each mouse. On 2, 5 and 7 days after transplantation, aqueous suspensions containing 100, 200 and 400 mg of the compounds to be tested per kg of body weight, respectively, are administered orally by means of a probe forcibly into stomach and the state of each mouse with lapse of time is observed. Antitumor effects are evaluated in terms of the survival term percentage T/C(%), obtained by dividing the average living days(T) of the group to which the compound to be tested is administered by the average living days(C) of the Control goup (ten mice only for the Control group) to which no compound is administered and being multiplied by 100. As the known standard substance, there is employed an antitumor agent for oral administration, namely FT-207[$N_1$-(2-tetrahydrofuranyl)-5-fluorouracil].

| Alkyl group in the compound tested ($N^4$—alkoxycarbonyl-1-$\beta$-D-arabinofurano-sylcytosine) | Dosage (mg/kg/day) | | |
|---|---|---|---|
| | 400 | 200 | 100 |
| | Survival term (T/C × 100%) | | |
| Butyl | 146 | 140 | 124 |
| Isobutyl | 148 | 142 | 122 |
| Pentyl | 152 | 146 | 130 |
| Hexyl | 158 | 144 | 134 |
| Cyclohexyl | 156 | 146 | 130 |
| Heptyl | 190 | 164 | 150 |
| Octyl | 178 | 160 | 148 |
| Nonyl | 255 | 188 | 168 |
| Decyl | 190 | 178 | 152 |

-continued

| Alkyl group in the compound tested (N⁴—alkoxycarbonyl-1-β-D-arabinofuranosylcytosine) | Dosage (mg/kg/day) | | |
|---|---|---|---|
| | 400 | 200 | 100 |
| | Survival term (T/C × 100%) | | |
| Undecyl | 268 | 194 | 172 |
| Dodecyl | 192 | 176 | 150 |
| Tridecyl | 252 | 185 | 166 |
| Myristyl | 198 | 180 | 164 |
| Pentadecyl | 250 | 182 | 164 |
| Palmityl | 190 | 172 | 154 |
| Heptadecyl | 182 | 160 | 146 |
| Stearyl | 156 | 144 | 135 |
| Nonadecyl | 154 | 142 | 132 |
| Eicosyl | 152 | 140 | 130 |
| Heneicosyl | 150 | 142 | 128 |
| Behenyl | 148 | 140 | 125 |
| Comparison (FT-207) | 142 | 130 | 115 |

Stability tests

The percentage remained after leaving a compound to be tested to stand at 50° C. for 30 days is measured using a high speed liquid chromatography. For comparison, stability of N⁴-acylarabinofuranosylcytosines is also measured under the same conditions.

| Stability test for N⁴—alkoxycarbonyl-arabinofuranosylcytosines | |
|---|---|
| Alkyl group in the compound tested (N⁴—alkoxycarbonyl-1-β-D-arabinofuranosylcytosine) | Percentage remained of principal ingredient after storage at 50° C. for 30 days (%) |
| Butyl | 95.4 |
| Isobutyl | 95.5 |
| Pentyl | 95.7 |
| Hexyl | 96.4 |
| Cyclohexyl | 96.9 |
| Heptyl | 97.5 |
| Octyl | 97.2 |
| Nonyl | 97.8 |
| Decyl | 97.3 |
| Undecyl | 98.0 |
| Dodecyl | 98.3 |
| Tridecyl | 98.2 |
| Myristyl | 98.1 |
| Pentadecyl | 98.5 |
| Palmityl | 98.4 |
| Heptadecyl | 98.1 |
| Stearyl | 98.3 |
| Nonadecyl | 98.2 |
| Eicosyl | 98.5 |
| Heneicosyl | 98.3 |
| Behenyl | 98.5 |

| Stability test for N⁴—acryl-arabinofuranosylcytosines | |
|---|---|
| Acryl group of the comparative test compound of N⁴—acylarabinofuranosylcytosine | Percentage remained of principal ingredient after storage at 50° C. for 30 days (%) |
| Butyryl | 87.2 |
| Valeryl | 87.4 |
| Caproyl | 88.1 |
| Heptanoyl | 88.8 |
| Caprylyl | 89.0 |
| Capryl | 89.4 |
| Lauroyl | 89.9 |
| Myristoyl | 90.3 |
| Pentadecanoyl | 91.8 |
| Palmitoyl | 92.2 |
| Margaroyl | 92.6 |
| Stearoyl | 92.5 |
| Nonadecanoyl | 92.7 |
| Arachidoyl | 92.4 |
| Heneicosanoyl | 92.8 |
| Behenoyl | 93.0 |

What is claimed is:

1. A N⁴-alkoxycarbonylarabinofuranosylcytosine represented by the formula:

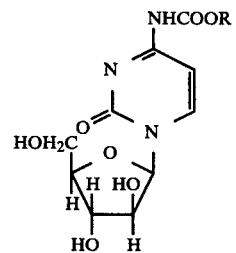

wherein R is an aliphatic hydrocarbon group having 4 to 22 carbon atoms.

2. A compound according to claim 1, wherein R is $C_{4-22}$ alkyl group.

3. A compound according to claim 2, wherein the alkyl group is a straight-chain $C_{4-22}$ alkyl group.

4. A compound according to claim 3, wherein the straight-chain alkyl group has 7 to 17 carbon atoms.

5. A compound according to claim 4, wherein the straight-chain alkyl group is n-nonyl, n-undecyl, n-tridecyl or n-pentadecyl.

6. A compound according to claim 2, wherein the alkyl group is a branched $C_{4-22}$ alkyl group.

7. A compound according to claim 6, wherein the branched alkyl group is isobutyl, isopentyl, isohexyl, isoheptyl, isooctyl or 2-ethylhexyl.

8. A compound according to claim 1, wherein R is a $C_{4-22}$ cycloalkyl group.

9. A compound according to claim 8, wherein the cycloalkyl group is cyclobutyl, cyclopentyl, cyclohexyl or cycloheptyl.

* * * * *